(12) United States Patent
Casper et al.

(10) Patent No.: US 7,520,607 B2
(45) Date of Patent: Apr. 21, 2009

(54) DEVICE FOR THE PREVENTION OF MELATIONIN SUPPRESSION BY LIGHT AT NIGHT

(75) Inventors: Robert Casper, Toronto (CA); Jennifer Wardrop, Toronto (CA); Jonathan Spilkin, Toronto (CA); Peter Solo, Toronto (CA)

(73) Assignee: Melcort Inc., Toronto, Ontario (CA)

( * ) Notice: Subject to any disclaimer, the term of this patent is extended or adjusted under 35 U.S.C. 154(b) by 0 days.

(21) Appl. No.: 10/525,958

(22) PCT Filed: Aug. 28, 2003

(86) PCT No.: PCT/CA03/01324

§ 371 (c)(1),
(2), (4) Date: Oct. 20, 2005

(87) PCT Pub. No.: WO2004/021071

PCT Pub. Date: Mar. 11, 2004

(65) Prior Publication Data

US 2006/0119954 A1 Jun. 8, 2006

Related U.S. Application Data

(60) Provisional application No. 60/406,306, filed on Aug. 28, 2002.

(51) Int. Cl.
*G02C 7/10* (2006.01)
*A61B 5/04* (2006.01)
(52) U.S. Cl. ...................... 351/163; 600/545
(58) Field of Classification Search .............. 351/163
See application file for complete search history.

(56) References Cited

U.S. PATENT DOCUMENTS

| 1,971,941 | A |   | 8/1934  | Pirani |
|-----------|---|---|---------|--------|
| 3,826,751 | A | * | 7/1974  | Laliberte ............... 252/587 |
| 4,719,248 | A | * | 1/1988  | Bambury et al. ......... 523/108 |
| 4,878,748 | A | * | 11/1989 | Johansen et al. ........... 351/44 |
| 4,952,046 | A | * | 8/1990  | Stephens et al. .......... 351/163 |
| 5,083,858 | A |   | 1/1992  | Girerd .................... 351/44 |
| 5,177,509 | A | * | 1/1993  | Johansen et al. ........... 351/44 |
| 5,274,403 | A |   | 12/1993 | Gott ....................... 351/44 |
| 5,304,212 | A |   | 4/1994  | Czeisler et al. |

(Continued)

FOREIGN PATENT DOCUMENTS

DE 197 29 719 A1 2/1998
EP 1 285 676 A2 2/2003

OTHER PUBLICATIONS

H. R. Wright et al : "Effect of Light Wavelength on Suppression and Phase Delay of the Melatonin Rhythm", Chronobiology International, vol. 18, No. 5, 2001, pp. 801-808.

(Continued)

*Primary Examiner*—Scott J Sugarman
*Assistant Examiner*—Dawayne A Pinkney
(74) *Attorney, Agent, or Firm*—Crowell & Moring LLP (57) ABSTRACT

The present invention provides a device for inhibiting melatonin suppressing light from reaching the retina. The device having means for selectively blocking light having a wavelength capable of suppressing melatonin production in a human.

22 Claims, 5 Drawing Sheets

U.S. PATENT DOCUMENTS

| | | | | |
|---|---|---|---|---|
| 5,400,175 | A | 3/1995 | Johansen et al. | 359/361 |
| 5,926,310 | A * | 7/1999 | Tamura et al. | 359/350 |
| 6,019,476 | A * | 2/2000 | Kirschner | 362/2 |
| 6,156,743 | A | 12/2000 | Whitcomb | |
| 6,638,963 | B1 | 10/2003 | Lewy et al. | |
| 2004/0246437 | A1* | 12/2004 | Ambler et al. | 351/163 |
| 2006/0009822 | A1 | 1/2006 | Savage et al. | |
| 2006/0106437 | A1 | 5/2006 | Czeisler et al. | |
| 2006/0119954 | A1 | 6/2006 | Casper et al. | |

OTHER PUBLICATIONS

Robert A. Hahn, "Profound Bilateral Blindness and the Incidence of Breast Cancer", Epidemiology Resources Inc., 1991, pp. 208-210, vol. 2.

Ichiro Kawachi, MD., et al., "Prospective Study of Shift Work and Risk of Coronary Heart Disease In Women", Circulation, 1995, pp. 3178-3182, vol. 92, The American Heart Association, Inc.

Johhni Hansen, "Increased Breast Cancer Risk Among Women Who Work Predominantly at Night", Epidemiology, 2001, pp. 74-77, vol. 12, No. 1, Lippincott Williams & Wilkins, Inc.

Scott Davis, et al., "Night Shift Work, Light at Night, and Risk of Breast Cancer", Journal of the National Cancer Institute, 2001, pp. 1557-1562, vol. 93, No. 20, Oxford University Press.

Eva S. Schernhammer, et al., "Rotating Night Shifts and Risk of Breast Cancer in Women Participating in the Nurses Health Study", Journal of the National Cancer Institute, Oct. 17, 2001, pp. 1563-1568, vol. 93, No. 20, Oxford University Press.

Sato Honma, et al., "Light Suppression of Nocturnal Pineal and Plasma Melatonin In Rats Depends on Wavelength and Time of Day", Neuorscience Letters, (1992), pp. 201-204, vol. 147, Elsevier Scientific Publishers Ireland, Ltd.

Tore Tynes, et al., "Incidence of Breast Cancer in Norwegian Female Radio and Telegraph Operators", Cancer Causes and Control, 1996, pp. 197-204, vol. 7, Rapid Science Publishers.

Eva S. Shernhammer, et al., "Night-Shift Work and Risk of Colorectal Cancer in the Nurses' Health Study", Brief Communication, Journal of the National Cancer Institute, Jun. 4, 2003, pp. 825-828, vol. 95, No. 11.

Daniel P. Cardinali, et al., "Melaton in Sleep Disorders and Jet-Lag", Neuorendocrinology Letters, 2002, pp. 9-13, vol. 23, ISSN 0172-7801.

Murray W. Johns, "A New Method for Measuring Daytime Sleepiness: The Epworth Sleepiness Scale", Sleep, American Sleep Disorders Association and Sleep Research Society, 1991, pp. 540-545.

J. A. Horne, et al., "A Self-Assessment Questionnaire to Determine Morningness-Eveningness in Human Circadian Rhythms", International Journal of Chronobiology, Jun. (1976), pp. 97-110, vol. 4, Gordon and Breach, Science Publishers Ltd.

Nalaka S. Gooneratne, et al., "The Validity and Feasibility of Saliva Melatonin Assessment in the Elderly", Journal of Pineal Research, 2003, pp. 88-94, vol. 34, Blackwell Munksgaard.

Alfred J. Lewy, et al., "The Endogenous Melatonin Profile as a Marker for Circadian Phase Position", Journal of Biological Rhythms, Jun. 1999, pp. 227-236, vol. 14, No. 3, Sage Publications, Inc.

Mendelson W. Bergmann, "Recovery After Sleep Deprivation in SCN-Lesioned Rats", Sleep, 2002, pp. A184-A186, vol. 25, American Academy of Sleep Medicine.

Dzhemaly S. Beniashvili, et al., "Effect of Light/Dark Regimen on N-Nitrosoethylurea-Induced Transplacental Carcinogensis in Rats", Cancer Letters 163, (2001), pp. 51-57, Elsevier Science Ireland Ltd., PII: S0304-3835(00)00673-X.

Johnni Hansen, "Light at Night, Shift Work, and Breast Cancer Risk", Journal of the National Cancer Institute, Oct. 17, 2001, pp. 1513-1515, vol. 93, No. 20, Editorials, Oxford University Press.

European Search Report dated Jun. 30, 2006.

Brainard, et al., "The Influence of Different Light Spectra on the Suppression of Pineal Melatonin Content in the Syrian Hamster, Department of Anatomy," Brain Research, 294 (1984) 333-339, Elsevier Science Publishers B.V., 1984.

Zeitzer, et al., "Photopic Tranduction Implicated in Human Circadian Entrainment," Neuroscience Letters 232 (1997) 135-183.

Akerstedt, T. et al., "Alertness-enhancing drugs as a countermeasure to fatigue in irregular work hours", Chronobiol Int, 1997, vol. 14, pp. 145-158.

Arai, Y. et al., "Critical exposure time for androgenization of the developing hypothalamus in the female rate", Endocrinology, vol. 82, pp. 1010-1014, 1968.

Armour, D. et al., "Melatonin in the treatment of insomnia in children and adolescents", Psychiatric Bulletin, (2004), vol. 28, pp. 222-224.

Barker, D., "In utero programming of chronic disease" Clin Sci, vol. 95, pp. 115-128, 1998.

Barker, D.J. et al., "Fetal nutrition and cardiovascular disease in adult life", Lancet, vol. 341, pp. 938-941, 1993.

Barrenetxe, J. Et al., "Physiological and metabolic functions of melatonin", J Physiol Biochem., 2004, vol. 60, pp. 61-72.

Benediktsson, R., "Glucocorticoid exposure in utero: new model for adult hypertension", Lancet, vol. 341, pp. 339-341, 1993.

Benloucif, S. et al., "Interactions between light and melatonin on the circadian clock of mice", J Biol Rhythms, 1999, vol. 14, pp. 281-289.

Benshoff, H.M. et al., "Suppression of pineal melatonin in Peromyscus leucopus by different monochromatic wavelengths of visible and near-ultraviolet light (UV-A)", Brain Res., 1987, vol. 420, pp. 397-402.

Blask, D.E. et al., "Melatonin-depleted blood from premenopausal women exposed to light at night stimulates growth of human breast cancer xenografts in nude rats", Cancer Res., 2005, vol. 65, pp. 11174-11184.

Blask, D.E. et al., "Growth and fatty acid metabolism of human breast cancer (MCF-7) xenografts in nude rats: impact of constant light-Induced nocturnal melatonin suppression", Breast Cancer Res Treat., 2003, vol. 79, pp. 313-320.

Cajochen, C. et al., "High Sensitivity of Human Melatonin, Alertness, Thermoregulation, and Heart Rate to Short Wavelength Light", J Clin Endocrinol Metab, 2005, vol. 90, No. (3), pp. 1311-1316.

Colligan, M.J. et al., "Shiftwork: Effects of social and family life. Shiftwork: Occupational Medicine" State of the Art Reviews, 1990, vol. 5, No. (2), pp. 315-322.

Czeisler, C.A. et al., "Exposure to bright light and darkness to treat physiologic maladaptation to night work", N Engl J Med, 1990, vol. 322, pp. 1253-1259.

Czeisler, C.A. et al., "Bright light induction of strong (type 0) resetting of the human circadian pacemaker", Science, 1989, vol. 244, pp. 1328-1333.

Dawson, D. et al., "Timed exposure to bright light improves sleep and alertness during simulated night shifts", Sleep, 1991, vol. 14, pp. 511-516.

Edwards, C.R. et al., "Dysfunction of placental glucocorticoid barrier: a link between the fetal environment and adult hypertension?", Lancet, vol. 341, pp. 355-357, 1993.

Frank, A.L., "Injuries related to shiftwork", Am J Prev Med, 2000, vol. 18, (45), pp. 33-36.

Gibson, E.S. et al., "The Impact of "Sleepiness" on Adolescent Students" Report of Population Health Grant 5555-15-1997-0000051, Health Canada, 1998-2002.

Gibson, E.S. et al., "'Sleepiness' is serious in adolescence: Two surveys of 3235 Canadian students" BMC Public Health, 2006, vol. 6, No. 116, pp. 1-9.

Goland, R.S. et al., "Elevated levels of umbilical cord plasma corticotropin-releasing hormone in growth-retarded fetuses", J Clin Endocrinol Metab, vol. 77, pp. 1174-1179, 1993.

Gustafsson, J.A. et al., "Sex steroid induced changes in hepatic enzymes", Annu Rev Physiol, vol. 45, pp. 51-60, 1983.

Hammer, F. et al., "Cortisol metabolism in hypertension", Best Pract Res Clin Endocrinol Metab., 2006, vol. 20, pp. 337-353.

Hattar, S. et al., "Melanopsin and rod-cone photoreceptive systems account for all major accessory visual functions in mice", Nature, 2003, vol. 424, pp. 76-81.

Healy, D. et al., "The clrcadian system and affective disorders: clocks or rhythms?", Chronobiol Intern, 1990, vol. 7, pp. 5-9.

Hoddes, E. et al., "Quantification of sleepiness: A new approach", Psychophysiol, 1973, vol. 10, pp. 431-436.

Horowitz, T.S. et al., "Efficacy of bright light and sleep/darkness scheduling in alleviating circadian maladaptation to night work" *Am J Physiol Endocrinol Metab*, 2001, vol. 281, pp. E384-E391.

Ishida, A. et al., "Light activates the adrenal gland: Timing of gene expression and glucocorticoid release", *Cell Metab.*, 2005, vol. 2, pp. 297-307 and Comment in: Cell Metab., Nov. 2005, vol. 2, No. (5), pp. 278-281.

Kayumov, L. et al., "A randomized, double-blind, placebo-controlled crossover study of the effect of exogenous melatonin on delayed sleep phase syndrome", Psychosom Med., 2001, vol. 63, pp. 40-48.

Kayumov, L. et al., "Blocking Low-Wavelength Light Prevents Nocturnal Melatonin Suppression with No Adverse Effect on Performance during Simulated Shift Work", *J Clin Endocrinol Metab.*, 2005, vol. 90, pp. 2755-2761.

Kayumov, L. et al., "Melatonin, sleep, and circadian rhythm disorders", *Semin Clin Neuropsychiatry*, 2000, vol. 5, pp. 44-55.

Khalsa, S.B. et al., "A phase response curve to single bright light pulses in human subjects" *J Physiol.*, 2003, vol. 549, pp. 945-952.

Krupp, L.B. et al, "The fatigue severity scale. Application to patients with multiple sclerosis and systemic lupus erythematosus", *Arch. Neurol.*, 1989, vol. 46, pp. 1121-1123.

Kubo, T. et al., "Prospective Cohort Study of the Risk of Prostate Cancer among Rotating-Shift Workers: Findings from the Japan Collaborative Cohort Study", *Am J Epidemiol*, 2006, vol. 164, No. 6 pp. 549-555.

Kubota, T. et al., "Effects of nocturnal bright light on saliva melatonin, core body temperature and sleep propensity rhythms in human subjects", *Neurosci Res.*, 2002, vol. 42, pp. 115-122.

Lindsay, R.S. et al., "Inhibition of 11-beta-hydroxysteroid dehydrogenase in pregnant rats and the programming of blood pressure in the offspring", *Hypertension*, vol. 27, pp. 1200-1204, 1996.

Lindsay, R.S. et al., "Prenatal glucocorticoid exposure leads to offspring hyperglycaemia in the rat: studies with the 11 β-hydroxysteroid dehydrogenase inhibitor carbenoxolone", *Diabetologia*, vol. 39, pp. 1299-1305, 1996.

Luna, T.D., "Air Traffic Controller Shiftwork: what are the implications for aviation safety? A review", *Aviat Space Environ Med*, 1997, vol. 68, pp. 69-79.

Mitler, M.M. et al., "Catastrophes, Sleep, and Public Policy: Consensus Report", *Sleep*, 1988, vol. 11, pp. 100-109.

Newnham, J.P. et al., "Maternal, but not fetal, administration of corticosteroids restricts fetal growth", *J Matern Fetal Med*, vol. 8, pp. 81-87, 1999.

Nowak, J.Z. et al., "Melatonin and its physiological and therapeutic properties", *Pharmacy World & Science*, vol. 20, No. 1, pp. 18-27, 1998.

Nyirenda, M.J. et al., "Glucocorticoid exposure in late gestation permanently programs rat hepatic phosphoenolpyruvate carboxykinase and glucocorticoid receptor expression and causes glucose intolerance in adult offspring", *J Clin Invest, vol. 15*, pp. 2174-2181, 1998.

Okawa, M. et al., "Circadian rhythm sleep disorders in adolescents: clinical trials of combined treatments based on chronobiology", *Psychiatry Clin Neurosci.*, 1998, vol. 52, pp. 483-490.

Owens, J., "Insomnia in Children and Adolescents", *Journal of Clinical Sleep Medicine*, 2005, vol. 1, pp. 454-e458.

Panda, S. et al., "Coordinated transcription of key pathways in the mouse by the circadian clock", *Cell*, 2002, vol. 109, pp. 307-320.

Perreau-Lenz, S. et al., "The Biological Clock: The Bodyguard of Temporal Homeostasis", *Chronobiology International*, 2004, vol. 21, No. 1, pp. 1-25.

Phelps, J., "Dark therapy for bipolar disorder using amber lenses for blue light blockade", *Med Hypotheses*, 2008, vol. 70, pp. 224-229.

Reinisch, J.M. et al., "Prenatal exposure to prednisone in humans and animals retards intrauterine growth", *Science*, vol. 202, pp. 436-438, 1978.

Revell, V. et al., "Alerting effects of light are sensitive to very short wavelengths", *Neuroscience Letters*, 2006, vol. 399, pp. 96-100.

Richter, H.G. et al., "The Circadian Timing System: Making Sense or day/night gene expression", 2004, *Biol Res*, vol. 37, pp. 11-28.

Rosa RR, Bonnet MH, Bootzin RR, Eastman CI, Monk T, Penn PE, Tepas DI, Walsh JK. Intervention factors for promoting adjustment to nightwork and shiftwork. *Occup Med* 1995 5: 391-414.

Runnebaum, I.B. et al., "Glucocorticoids Inhibit Cell Death in Ovarian Cancer and Up-regulate Caspase Inhibitor cIAP2", *Clin Cancer Res*, 2005, vol. 11, pp. 6325-6332.

Schrey, M.P. et al., "Bombesin and glucocorticoids stimulate human breast cancer cells to produce endothelin, a paracrine mitogen for breast stromal cells", *Cancer Research*, 1992, vol. 52, pp. 1786-1790.

Shanahan, T.L. et al., "Resetting the melatonin rhythm with light in humans", *J Biol Rhythms*, 1997, vol. 12, pp. 556-567.

Shirayama, M. et al., "The psychological aspects of patients with delayed sleep phase syndrome (DSPS)", *Sleep Med.*, 2003, vol. 4, No. (5), pp. 427-433.

Smith, L. et al., "Increased injuries on night shift", *Lancet*, 1994, vol. 344, pp. 1137-1139.

Sookoian, S. et al., "Effects of rotating shift work on biomarkers of metabolic syndrome and inflammation", *J Intern Med*, 2007, vol. 261, pp. 285-292.

Steckler, T. et al., "Glucocorticoids and depression" *Baillieres Best Pract Res Clin Endocrinol Metab.*, 1999, vol. 13, pp. 597-614.

Sunter, D., "Working Shift", Perspectives, Statistics Canada (Catalogue 75-001E), Spring 1993, pp. 16-23.

Thapan, A. et al., "An action spectrum for melatonin suppression: evidence for a novel non-rod, non-cone photoreceptor system in humans", *J Physiol*, 2001, vol. 535, pp. 261-267.

Tuunainen, A. et al., "Depression and endogenous melatonin in post menopausal women", *J Affect Disord.*, 2002, vol. 69, No. (1-3), pp. 149-158.

Van Dongen, H.P., "Shift work and inter-individual differences in sleep and sleepiness", *Chronobiol Int.*, 2006, vol. 23, pp. 1139-1147.

Van Dongen, P.A. et al., "The cumulative cost of additional wakefulness: dose-response effects on neurobehavioral functions and sleep physiology from chronic sleep restriction and total sleep deprivation", *Sleep*, 2003, vol. 26, No. 2, pp. 117-126.

Ward, R.M. "Pharmacologic enhancement of fetal lung maturation", *Clin Perinatol*, vol. 21, pp. 523-542, 1994.

Wetterberg, L., "Clinical importance of Melatonin", *Prog Brain Res.*, 1979, vol. 52, pp. 539-534.

Wetterberg, L., "Chapter 3. In: Shaffi M, Shaffi SL, eds. *Melatonin in adult depression*. Washington DC, MD", American Psychiatric Press Inc.; 1998, pp. 43-79.

Whitmore, J.N. et al., "Psychophysiological effects of a brief nocturnal light exposure", *J Hum Ergol.*, 2001, vol. 30, pp. 267-272.

Wirz-Justice, A. "Biological rhythm disturbances in mood disorders", *Int Clin Psychopharmacol.* 2006, vol. 21 Suppl 1: S11-5.

Wolfson, A.R. et al., "Early school start times affect sleep and daytime functioning in adolescents", Sleep Research, 1996, vol. 25, pp. 117.

Wolfson, A.R. et al., "Sleep schedules and daytime functioning in adolescents", Child Dev, Aug. 1998, vol. 69, pp. 875-887.

Wood, P.A. et al., "Circadian clock coordinates cancer cell cycle progression, thymidylate synthase, and 5-fluorouracll therapeutic index", *Mol Cancer Ther.*, 2006, vol. 5, pp. 2023-2033.

Zeitzer, J.M. et al., "Sensitivity of the human circadian pacemaker to nocturnal light: melatonin phase resetting and suppression", *J Physiol.*, 2002, vol. 526, pp. 695-702.

International Search Report dated Apr. 29, 2008 (Four (4) pages).

Written Opinion of The International Searching Authority dated Apr. 29, 2008 (Nine (9) pages).

\* cited by examiner

DEVICE FOR THE PREVENTION OF MELATIONIN SUPPRESSION BY LIGHT AT NIGHT

FIELD OF THE INVENTION

The present invention relates to a device for inhibiting melatonin suppressing light and in particular to a device for preventing the suppression of melatonin levels that normally occurs upon exposure to broad spectrum wavelength light at night.

BACKGROUND OF THE INVENTION

A form of environmental pollution that has attracted recent interest is light pollution, in the form of light trespass, up-light that obscures the night sky and glare or side-light that blinds at night. In addition, there is recent evidence that exposure to light at night may have detrimental effects on the health of both animals and humans. Melatonin secretion from the pineal gland has been implicated in the etiology of these adverse health effects of night light exposure.

Melatonin, N-acetyl-5-methoxytryptamine, is the principal hormone of the pineal gland, and mediates many biological functions, particularly those that are controlled by the duration of light and darkness. Melatonin is synthesized from tryptophan through serotonin, which is N-acetylated by the enzyme n-acetyl transferase or NAT, and then methylated by hydroxyindol-O-methyl transferase. The enzyme NAT is the rate-limiting enzyme for the synthesis of melatonin, and is increased by norepinephrine at the sympathetic nerve endings in the pineal gland. Norepinephrine is released at night or in the dark phase from these nerve endings. Thus, melatonin secretion is controlled mainly by light and dark phases.

The secretion of melatonin in the human is circadian, with high levels at night and low levels in the morning. The light/dark cycle is a pervasive and prominent Zeitgeber of the regulation of circadian timing system: in the presence of light, the output from the Retino-Hypothalamic Tract inhibits the melatonin synthesis, whereas darkness stimulates it.

Like myriads of circadian rhythms in mammals (drinking and feeding, wake-sleep cycle, temperature, cortisol, corticosterone etc.), the melatonin rhythm is generated by an endogenous pacemaker located in the anterior hypothalamic suprachiasmatic nuclei (SCN). In humans, the circadian rhythm for the release of melatonin is closely synchronized with the habitual hours of sleep. Typically, melatonin secretion starts at 2100 hrs (9 pm) and increases to a peak at 0200 hr (2 am) and then falls to a nadir about 0600 hr (6 am). However, a curious characteristic of the melatonin rhythm is that it can be acutely interrupted by exposure to light. It has been shown that light exposure in the early subjective night delays the timing of the circadian clock while light exposure in the late subjective night advances the timing of the clock. Exposure to light at either time suppresses melatonin secretion.

The melatonin secretion rhythm changes for shift workers, who eventually have a different rise and fall depending on their "normal" time of resting. Travelers through different time zones suffer from so-called jet lag that in most part is related to their circadian rhythm of melatonin being out of synchrony with the local clock time. Light suppression of melatonin can occur very quickly in the dark phase with secretion returning rapidly following the cessation of light. Exposure to light in the middle of the dark period results in suppression of melatonin levels of up to 85%.

All of melatonin's functions have yet to be defined, but this hormone appears to: 1) Synchronize the circadian rhythms of the body, 2) Stimulate immune function, 3) Inhibit growth of cancer cells in vitro, and 4) Reduce the progression and promotion of cancer in vivo.

Some forms of cancer, for example, certain breast cancers and prostate cancers, are hormone dependent. In the test tube, melatonin inhibits the growth of breast tumor cells, and in animals blocks the growth of breast cancer. Melatonin has recently been demonstrated to be a potent antioxidant by scavenging highly reactive hydroxyl radicals, and in vitro protects DNA from free radical damage. This effect is concentration dependent. Antioxidant activity may be one of the ways that melatonin helps to prevent cancers. In animals, removal of the pineal gland can increase the growth of some cancers. Conversely, women with profound bilateral blindness have high melatonin levels and a significantly decreased incidence of cancer of the breast, as described in Hahn R A, Profound bilateral blindness and the incidence of breast cancer, Epidemiology 1991;2:208-10.

Clinical studies have demonstrated that shift-workers who work part of, or the whole of the night, in a lighted environment may have increased rates of heart disease and cancer, as described in Kawachi I, et al., Prospective study of shift work and risk of coronary heart disease in women, Circulation 1995;92:3178-82 and Hansen J, Increased breast cancer risk among women who work predominantly at night, Epidemiology 2001;12:74-7.

Two epidemiologic studies have determined a link between exposure to light at night and an increased risk of breast cancer. In one study described in Davis S, et al., Night shift work, light at night, and risk of breast cancer, J Natl Cancer Inst 2001;93:1557-62 case patients with breast cancer (n=813), aged 20-74 years, were compared with control subjects (n=793) identified by random-digit dialing and age matched. An in-person interview was used to gather information on sleep habits and bedroom lighting environment in the 10 years before diagnosis and lifetime occupational history. The authors found that breast cancer risk was increased among subjects who frequently did not sleep during the period of the night when melatonin levels are typically at their highest (OR=1.14 for each night per week; 95% CI=1.01 to 1.28). Risk did not increase with interrupted sleep accompanied by turning on a light. There was an indication of increased risk among subjects with the brightest bedrooms. Graveyard shiftwork was associated with increased breast cancer risk (OR=1.6; 95% CI=1.0 to 2.5), with a trend of increased risk with increasing years and with more hours per week of graveyard shift work (P=0.02). The results of this study provided evidence that exposure to light at night may be associated with the risk of developing breast cancer. The authors speculated that exposure to light at night may increase the risk of breast cancer by suppressing the normal nocturnal production of melatonin by the pineal gland, which, in turn, could increase the release of estrogen by the ovaries.

Data from the Nurses Health Study was also analyzed to search for a link between light at night and breast cancer risk. The authors investigated the relationship between breast cancer and working on rotating night shifts during 10 years of follow-up in 78 562 women from the Nurses' Health Study, described in Schernhammer E S, et al., Rotating night shifts and risk of breast cancer in women participating in the nurses' health study, J Natl Cancer Inst 2001;93:1563-8. Information was ascertained in 1988 about the total number of years during which the nurses had worked rotating night shifts of three or more days per month. From June 1988 through May 1999, 2441 incident breast cancer cases were documented.

The authors observed a moderate increase in breast cancer risk among the women who worked 1-14 years or 15-29 years on rotating night shifts (multivariate adjusted RR=1.08 [95% CI=0.99 to 1.18] and RR=1.08 [95% CI=0.90 to 1.30], respectively). The risk was further increased among women who worked 30 or more years on the night shift (RR=1.36; 95% CI=1.04 to 1.78). The test for trend was statistically significant (P=0.02). They concluded that women who work on rotating night shifts with at least three nights per month, in addition to days and evenings in that month, appear to have a moderately increased risk of breast cancer after extended periods of working rotating night shifts.

In all of the clinical studies, the adverse effect of light exposure at night on cancer risk was thought to act through suppression of melatonin levels. A recent study examined the effects of different wavelengths of light on melatonin suppression and phase shifting of the salivary melatonin rhythm in the human, described in Wright H R, and Lack L C, Effect of light wavelength on suppression and phase delay of the melatonin rhythm, Chronobiol Int 2001;18:801-8. The wavelengths compared were 660 nm (red), 595 nm (amber), 525 mn (green), 497 nm (blue/green), and 470 nm (blue) and light of each wavelength was administered using light-emitting diodes equated for irradiance of 130 muW/cm2. Fifteen volunteers participated in all five wavelength conditions and a no light control condition, with each condition conducted over two consecutive evenings. Half-hourly saliva samples were collected from 19:00 to 02:00 on night 1 and until 01:00 on night 2. Light was administered for the experimental conditions on the first night only from midnight to 02:00. Percentage melatonin suppression on night 1 and dim light melatonin onset (DLMO) for each night were calculated. The shorter wavelengths of 470, 497, and 525 nm showed the greatest melatonin suppression, 65% to 81%. The shorter wavelengths also showed the greatest DLMO delay on night 2, ranging from 27 to 36 min. There was much less suppression of melatonin by higher wavelengths, such as red or amber light.

In a rat model, exposure to light of different wavelengths also resulted in similar findings regarding melatonin suppression, as described in Honma S, et al., Light suppression of nocturnal pineal and plasma melatonin in rats depends on wavelength and time of day, Neurosci Lett 1992;147:201-4. Effects of light on pineal gland and plasma melatonin were examined in Wistar and Long-Evans rats at the $4^{th}$ hour into the dark phase (light off from 18.00 h to 06.00 h) using lights of two different monochromatic wavelengths but with the same irradiance. The green light pulse (520 nm) given at 24.00 h suppressed the pineal and plasma melatonin to the day-time level for at least 2 h, while the red light (660 nm) pulse suppressed pineal melatonin only transiently and did not suppress the plasma melatonin at all.

Animal studies, in Beniashvili et al, Effect of light/dark regimen on N-nitrosoethylurea-induced transplacental carcinogenesis in rats. Cancer Lett., 2001 Feb. 10; 163(1):51-7, have shown that constant exposure to light significantly promotes transplacental carcinogenesis. Observational studies have associated night-shift work with an increased risk of breast and colorectal cancers as shown in for example Tynes et al., Incidence of breast cancer in Norweigan female radio and telegraph operators. Cancer Causes Control. 1996 Mar. 7(2):197-204; Hansen, J., Light at night, shiftwork, and breast cancer risk. J. Natl Cancer Inst. 2001 Oct. 17; 93(20):1513-5; and Schernhammer et al., Night-shift work and risk of colorectal cancer in the nurses' health study. J Natl. Cancer Inst. 2003 Jun. 4;95(11):825-8. Furthermore, melatonin has been shown to be a free-radical scavenger and antioxidant, and conditions that involve free radical damage may be aggravated by light suppression of melatonin levels (Reiter, Potential biological consequences of excessive light exposure: melatonin suppression, DNA damage, cancer and neurodegenerative diseases. Neuroendocrinol Lett 2002 Jul. 23 Suppl 2:9-13). These findings suggest that shift-workers may have an increased danger of developing various forms of cancer due to a repetitive exposure to light at night.

Therefore, studies in humans and in rats both demonstrated that different wavelengths of light during the dark phase suppress melatonin levels differentially. White light and short wavelength light (green and blue) suppress melatonin to the greatest degree, while longer wavelengths of light (eg. red) have little or no melatonin suppression. It is therefore desirable to provide an optical filter that selectively blocks light of a wavelength capable of suppressing melatonin levels in a human that can be used by people who are exposed to melatonin suppressing light at peak melatonin production times.

BRIEF DESCRIPTION OF THE DRAWINGS

The invention may be better understood by the attached description and may be further illustrated by the figures, in which.

SUMMARY OF THE INVENTION

In a broad aspect the present invention provides a device for inhibiting melatonin suppressing light. The device includes a means for selectively blocking light of a wavelength capable of suppressing melatonin production in a human.

In one embodiment the present invention provides an optical filter, and the use thereof, designed to prevent melatonin suppression by light at night by preventing light of certain wavelengths, known to maximally suppress melatonin, from reaching the retina of the eye.

In another embodiment the present invention provides a lens, and the use thereof, that includes an optical filter that selectively blocks light of a wavelength capable of suppressing melatonin production in a human. The lens being suitable for use in eyewear for humans who are exposed to melatonin suppressing light at peak melatonin production times.

In another embodiment the present invention provides a lens having an optical filter that is operable to block light having a wavelength that suppresses melatonin production, and a polarizing layer.

DETAILED DESCRIPTION OF THE INVENTION

This present invention may be accomplished by various means. The following provides a definition for some of the terms used in the specification:

Eyewear is used as a broad term to encompass such items as eyeglasses, goggles, contact lenses and the like, that are used in connection with the eyes of a user to either shield/protect the eyes from harmful substances, for example chemicals in the context of goggles or to enhance the eyesight of the user, for example contact lenses. It will be understood that the term "eyewear" is not limited to the above examples, and describes any device used in connection with the eyes that contains a viewing window of sorts.

Melatonin suppressing light is light that has a wavelength that suppresses the production or secretion of melatonin in a human. Melatonin suppressing light is preferably, but not limited to, light having a wavelength in the green spectrum.

Substantially transmitting, when used in terms of wavelength of light, is defined as transmitting more than 1 percent of the incident radiation at each and every wavelength.

Substantially blocking, when used in terms of wavelength of light, is defined as blocking over 50 percent of the incident wavelength at each and every wavelength.

As discussed above, in one embodiment the present invention provides a device for inhibiting melatonin suppressing light. The device has means for selectively blocking light having a wavelength capable of suppressing melatonin levels in a human. The means for selectively blocking light preferably blocks a sufficient amount of the light, having a wavelength capable of suppressing melatonin level, to result in the prevention of at least about 50% of the melatonin suppression. The device may be, but is not limited to, for example eyewear, a light bulb, a light cover, a lens, or any other device that may be utilized for the purpose of preventing light of wavelengths that suppress melatonin levels in a human. In use, the device prevents light of wavelengths that suppress melatonin levels from reaching the retina of a human, thereby preventing suppression of melatonin levels in the human.

In another embodiment the present invention provides an optical filter that selectively blocks light of a wavelength capable of suppressing melatonin production in a human. The optical filter preferably blocks a sufficient amount of the light, having a wavelength capable of suppressing melatonin level, to result in the prevention of at least about 50% of the melatonin suppression. Another embodiment of the present invention provides a lens that includes an optical filter that selectively blocks light of a wavelength capable of suppressing melatonin production in a human. The lens being suitable for use in eyewear for humans who are exposed to melatonin suppressing light at peak melatonin production times. As will be understood by a person skilled in the art, the lens may be made from any material that is suitable to be used in eyewear, examples of such material include, but are not limited to, glass or plastic.

In another embodiment the present invention provides a lens having an optical filter that is operable to block light having a wavelength that suppresses melatonin production in a human, and a polarizing layer. The polarizing layer being operable to selectively absorb reflected glare in one direction. It will be understood by a person skilled in the art that the polarizing layer may have any form that is suitable to be used in a lens. For example, the polarizing layer may be a polarized film that can be laminated to the surface of the lens, such as PP10 polarized lens material produced by Polaroid. Other suitable embodiments of the polarizing layer will be known by a person skilled in the art.

In a further embodiment the lens may also include an ultraviolet light absorber laminated to at least one side of the lens or the lens may be treated or coated with an ultra violet filter such as an ultra violet light blocking dye. The ultraviolet light absorber being operable to absorb UV rays and preferably operable to absorb 100% of harmful UV rays.

The embodiments described above provide a lens that is operable to prevent light of certain melatonin suppressive wavelengths from reaching the retina of the eye.

In another embodiment of the invention, an optical filter may be applied to the surface of an incandescent or fluorescent light bulb to block light of specific short wavelengths from being emitted. The optical filter that is used preferably selectively blocks light of a wavelength capable of suppressing melatonin production in a human.

Another embodiment is the application of an optical filter, to block light of specific short wavelengths, into the semi-opaque lens of a nightlight. The optical filter being capable of selectively blocking light of a wavelength capable of suppressing melatonin production in a human.

Studies to date have shown that the incidence of breast cancer is increased in night shift workers, an effect attributed to suppression of the night melatonin secretion peak by light exposure. The present invention provides a lens that can be incorporated into eyewear that a night shift worker can wear in order to prevent the melatonin suppressing wavelengths from reaching their retinas. By preventing the melatonin suppressing light from reaching the retina, melatonin will continue to be produced thereby reducing the risks to the worker that are associated with a lack of melatonin production, for example reducing the possible risk of breast cancer.

An alternative embodiment of the present invention is a light cover for use in conjunction with a light source. The light cover may include an optical filter that is operable to selectively block light from the light source having a wavelength capable of suppressing melatonin production in a human. The cover being operable to releasably attach to the light source to channel the light emitted from the light source through the cover. It will be understood by a person skilled in the art that the cover may be any shape or form as long as it is operable to cover the light source that it is to be used with, for example if the light source is an oblong strip light, then the cover is preferably oblong and of a size that will fit around the light source to contain the light source therein. By containing the light source within the cover the light emitted from the light source must be channeled through the cover, and therefore all light having a wavelength capable of suppressing melatonin production in a human will be blocked.

The light cover may also be permanently attached to the light source, for example the light cover may be a coating on the light source, or the light source may be manufactured from a material that selectively blocks light having a wavelength capable of suppressing melatonin production in a human.

An additional benefit of the invention may include the reduction of the incidence and severity of jet lag in travelers across multiple time zones where out of phase exposure to light may disturb the normal circadian rhythm of melatonin.

The following example illustrates one embodiment of the invention. It will be understood that the present invention is not limited to the example provided.

EXAMPLE 1

Figure 1:
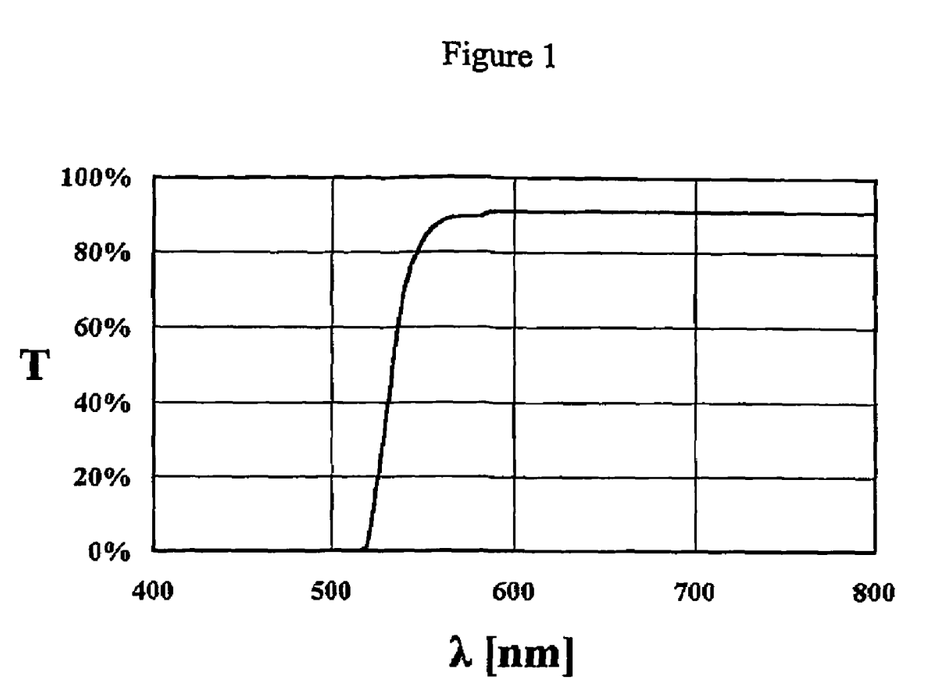
FIG. 1 illustrates the technical characteristics of the yellow lenses described in example 1.
Figure 2A:
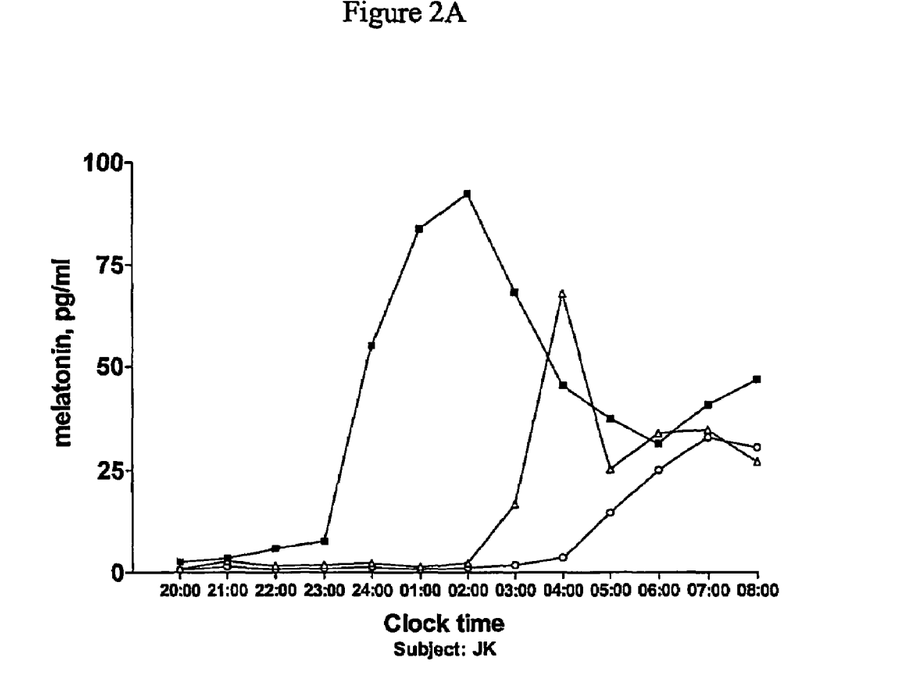
FIGS. 2A-C illustrates the characteristic effects of bright and filtered light on endogeneous melatonin secretion by three male patients, as described in example 1.
Figure 2B:
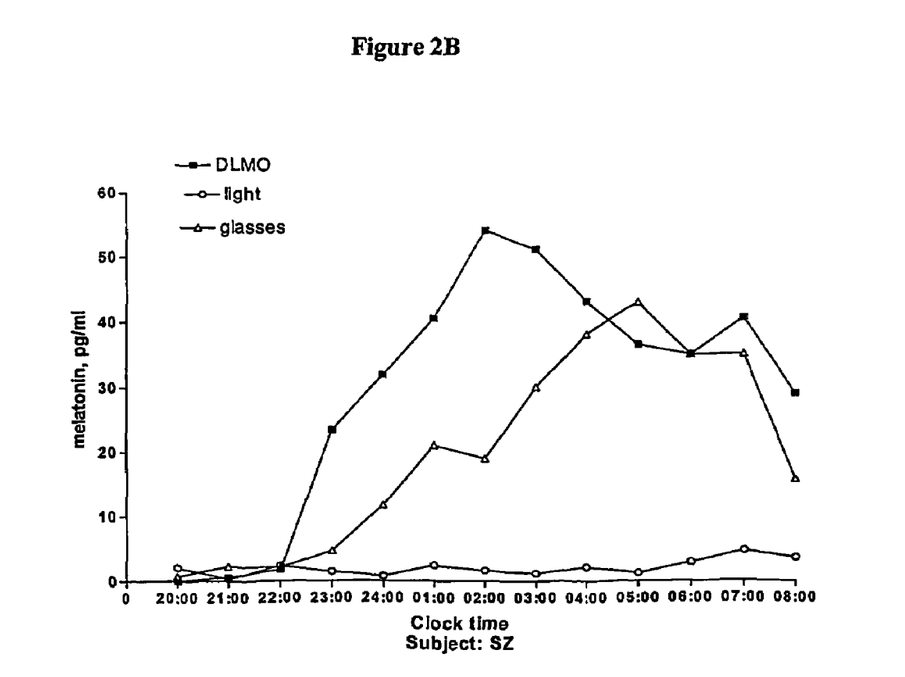
Figure 2C:
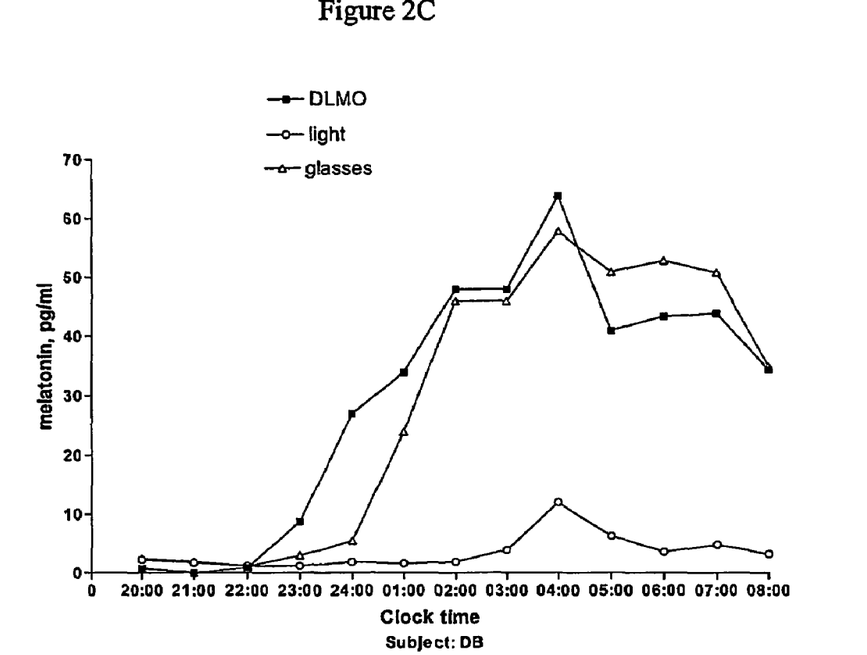
Figure 2D:
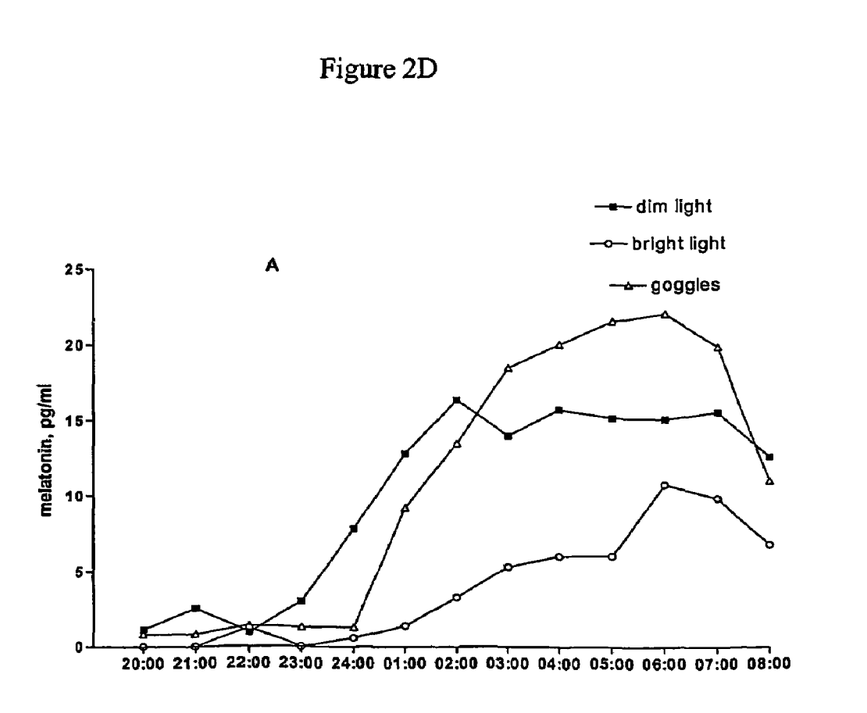
FIGS. 2D-E illustrates the characteristic effects of bright and filtered light on endogeneous melatonin secretion by two female patients, as described in example 1.
Figure 2E:
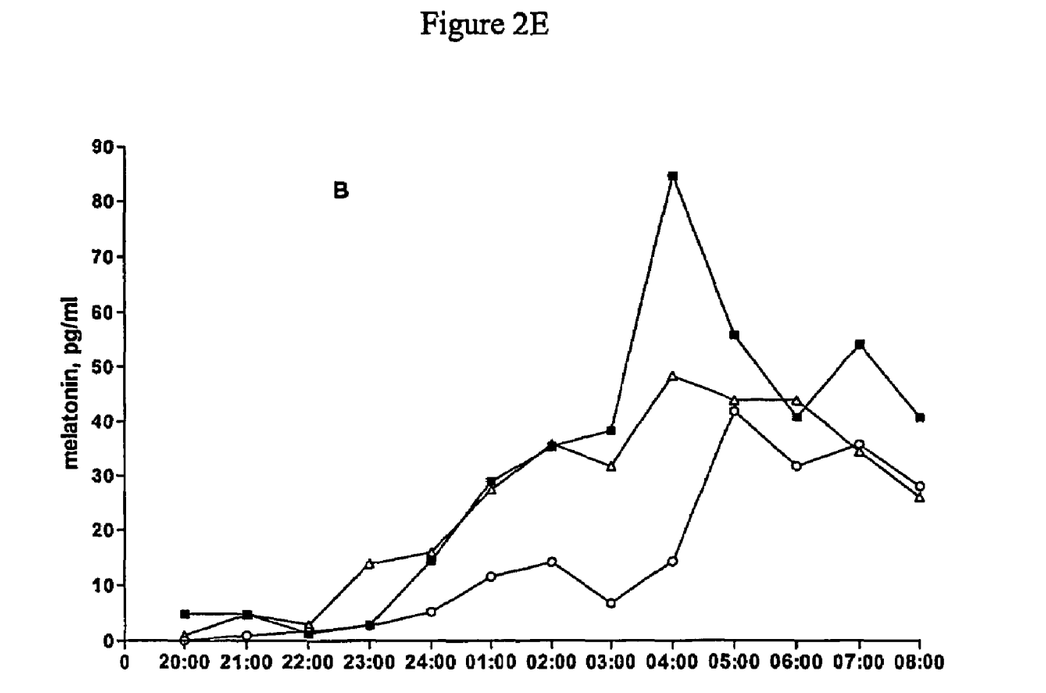

A study was undertaken to measure the impact on melatonin production of one type of yellow lens. A yellow filter lens was provided that allowed selective exclusion of all wavelengths below 530 nm while maintaining relatively good color recognition and a visual light transmittance in daylight of approximately 63% and a visual light transmittance in nightlight of approximately 73%. FIG. 1 illustrates the technical characteristics of the lenses having an edge at +/−530 nm, and above 530 nm filters out approximately 8% of longer wavelengths.

In the study a total of 6 healthy young males and 2 healthy young females (mean age 22.5±1.5) participated. The inclusion and exclusion criteria for this study were implemented to discourage biased data resulting from external factors. All subjects underwent a psychiatric and sleep assessment to rule out significant psychopathology and sleep disruption. All subjects scored less than 7 on the Epworth Sleepiness Scale as described in Johns, A new method for measuring daytime sleepiness. Sleep 1991 Dec. 14(6):540-5, and scored in the normal range on the Morningness/Eveningness questionnaire as described in Home and Ostberg, A self-assessment questionnaire to determine morningness-eveningness in human circadian rhythms. Int. J. Chronobiol. 1976; 4(2):97-110, a subjective measure of their circadian rhythm. Subjects were rejected if they had experienced sleep and circadian rhythm disorders, excessive daytime sleepiness, eye disease, depression, psychotic illness, a history of cancer, or shift-work in the past year.

During the study, subjects were asked to stay awake overnight at a Sleep Research Clinic for 3 non-consecutive nights over a two-week period. Prior to each night of the study, subjects were asked to complete a previous night sleep inventory (PNSI) to ensure that their quality of sleep was not deficient The first night, melatonin production measured (in saliva) under dim light (<50 1x) conditions established each individual's circadian profile of melatonin secretion, unaffected by light exposure. Saliva specimens provide a non-invasive and practical method for melatonin assessment with high validity as described in Gooneratne et al., The validity and feasibility of saliva melatonin assessment in the elderly. J. Pineal Res. 2003 March; 34(2):88-94.

The Dim Light Melatonin Onset (DLMO) test, as described in Lewy et al, The endogenous melatonin profile as a marker for circadian phase position. J Biol Rhythms. 1999 June; 14(3):227-36; Kayumov et al, Exogenous melatonin shifts dim light melatonin onset in post-traumatic delayed sleep phase syndrome. Sleep 2002; 25: 18, was used as a marker of circadian phase, and was the time of the first saliva melatonin level to cross the DLMO threshold. The threshold was defined as 20% of the maximum raw value of endogenous melatonin.

The subjects spent 12 hours awake from 20:00 h to 08:00h in the sleep laboratory while hourly data was collected. The results of the DLMO testing provided a baseline for comparison of melatonin levels during the other interventions.

The subjects were randomly assigned to wear the yellow filter lenses incorporated into goggles on either the second or third night. On the alternate night, the subjects were exposed to the bright light without wearing goggles. On all nights, 13 saliva samples were collected at regular one-hour intervals beginning at 20:00 h (8:00pm). Subjects were placed in a well lit room (800 1x) designed to mimic a shift-work environment. The exact luminescence of the rooms was determined using a luxometer.

Due to individual variability in DLMO and acute phase shifting effects of light on melatonin secretion profiles, the clock time was converted to circadian time (CT). For this purpose, the beginning of melatonin production was referenced by designating the baseline DLMO as CT 14, as described in Ahmed et al, Phase response curve of low-intensity green light in winter depressives. Sleep Research 1995; 24: 508. This technique provided the ability to compare the hormonal status of each individual at the same circadian time in three different conditions.

Moreover, it was assumed that darkness is an ideal environment for maximum melatonin production and therefore, relative values of melatonin in light conditions (with or without goggles) compared to designated 100% production in the dark were used. Another reason to use relative values was the large interpersonal variability in absolute melatonin levels since it is well recognized that there are low and high melatonin secretors.

Repeated measures analysis of variance (MANOVA) was used to determine the statistical significance of melatonin values in the three different conditions. Statistically significant results detected by analysis of variance (p<0.05) were further analyzed by using Tukey post hoc paired comparisons using the Statistical Package for the Social Sciences software (SPSS, version 11.5, for Windows.

Saliva specimens were collected using the Sali-Saver™ (ALPCO—American Laboratory Products Company, N.H., USA). The Sali-Saver™ consists of a small cotton roll that is placed between the cheek and the gum for 3-5 min in order to collect saliva specimen (up to 2 ml can be collected at a time). Saliva specimens were analyzed immediately after collection of the last sample. Saliva melatonin was determined by Direct Saliva Melatonin ELISA kit from Buhlman Laboratories (Allschwil, Switzerland). Aliquots of at least 200 µl of centrifuged saliva from each collection time were used for the analysis. Saliva specimens from a given subject were run with the same assay kit. Quality control was assessed by using a low and high melatonin standard included in the kit. Assay functional sensitivity was 1.3 pg/ml, the maximum intra-assay and inter-assay coefficients of variability were 6.5% (n=12) and 11.3% (n=12), respectively (in the range of concentrations of melatonin between 1 and 81 pg/ml).

The study results showed that all subjects wearing yellow lenses exhibited a melatonin secretion profile similar to their dim light pattern throughout the night. In contrast, bright light drastically suppressed melatonin production. Exposure to bright light and filtered light caused a phase delay in endogenous melatonin secretion, although the latter condition induced a less pronounced shift. FIG. 2A-E displays characteristic effects of bright and filtered light on endogenous melatonin secretion in 3 male subjects (Figures A-C) and 2 female subjects (Figures D and E). The results under the dim light condition (■) represent normal melatonin production. All subjects demonstrated preserved melatonin secretion in filtered light (▲) similar to the profile obtained in dim light, although there was a noticeable phase delay under both light conditions.

Figure 3:
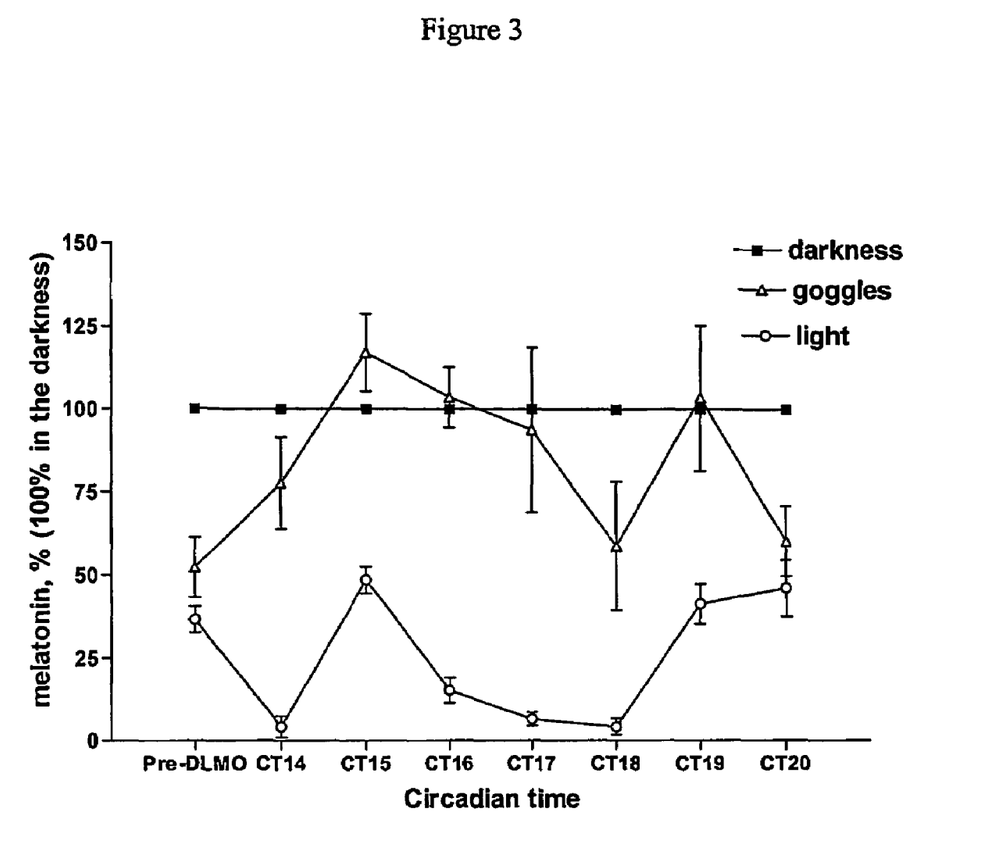
FIG. 3 illustrates relative values of melatonin secretion during dim-light, exposure to bright-light and exposure to light protected by yellow lenses as described in example 1.

Conversion of the clock time into circadian time reduced samples available for analysis (from 13 to 8): pre-DLMO baselines and CT14 through CT20 melatonin levels. Analysis of variance (MANOVA) showed that suppression of melatonin levels at all data collection points (except at Pre-DLMO) did not occur when yellow lenses were worn (Pre-DLMO F=4.6, p>0.05; CT14 F=16.4, p<0.0001; CT15 F=19.2, p<0.0001; CT16 F=37.2, p<0.0001; CT17 F=10.4, p=0.001; CT18 F=19.7, p<0.0001; CT20 F=26.3, p<0.0001). FIG. 3 illustrates relative values of melatonin secretion during dim-light, exposure to bright light, and exposure to light protected by yellow lenses for the entire group.

The data illustrates that wearing light-filtering goggles to block wavelengths less than 530 nm allows close to normal melatonin onset and peak secretion in subjects during night-time exposure to bright light.

While the invention has been described with reference to certain embodiments thereof, it will be understood that changes and modifications may be made by those of ordinary skill in the art within the scope and spirit of the following claims.

We claim:

1. A device for inhibiting melatonin suppression by light comprising: means for selectively blocking more than 50 percent of incident wavelengths of light having a wavelength range less than at or about 530 nm, while transmitting more than 50 percent of non-blocked wavelengths of light, wherein the device inhibits the light-induced suppression of melatonin production by light exposure when used at night.

2. A device according to claim 1, wherein the means for selectively blocking light is an optical filter.

3. A device according to claim 2, comprising the optical filter which includes a polarizing layer.

4. A device according to claim 1, wherein the device further comprises an ultraviolet light absorber.

5. A device according to claim 2, comprising at least one of eyewear, a lightbulb, a light cover and a lens.

6. A lens operable by a user who is exposed to light at peak melatonin production times at night, the lens comprising an optical filter operable to selectively block more than 50 percent of incident wavelengths of light having a wavelength range less than at or about 530 nm, while transmitting more than 50 percent of non-blocked wavelengths of light, wherein the lens inhibits the suppression of melatonin production of by light when used at peak melatonin production times.

7. A lens according to claim 6, wherein the lens is incorporated in eyewear.

8. A lens according to claim 7, wherein the eyewear is selected from the group consisting of spectacles, goggles, contact lenses and safety glasses.

9. A light device comprising an optical filter operable to selectively block more than 50 percent of incident wavelengths of light from the light device having a wavelength that suppresses melatonin production in a human of less than at or about 530 nm, while transmitting more than 50 percent of non-blocked wavelengths of light.

10. A light device according to claim 9, wherein the light device is chosen from an incandescent light source, a fluorescent light source or any other artificial light source.

11. A light device according to claim 9, wherein the optical filter is a coating on at least one surface of the device.

12. A light cover for use with a light device, the cover comprising: an optical filter operable to selectively block more than 50 percent of incident wavelengths of light from the light device having a wavelength that suppresses melatonin production in a human of less than at or about 530 nm, while transmitting more than 50 percent of non-blocked wavelengths of light, the cover being operable to releasably attach to the light source to channel the light emitted from the light source therethrough.

13. A method for inhibiting melatonin suppression by light in a human comprising providing the device according to claim 2 during peak melatonin production times thereby selectively blocking more than 50 percent of incident wavelengths of light having a wavelength range less than at or about 530 nm, while transmitting more than 50 percent of non-blocked wavelengths of light, the device being operable to selectively block light, having a wavelength range less than at or about 530 nm, from reaching the retina in a human for inhibiting melatonin suppression by light.

14. A method for inhibiting melatonin suppression by light in a human comprising providing the device according to claim 1, during peak melatonin production times thereby selectively blocking more than 50 percent of incident wavelengths of light having a wavelength range less than at or about 530 nm, while transmitting more than 50 percent of non-blocked wavelengths of light, the device being operable to selectively block light, having a wavelength range less than at or about 530 nm, from reaching the retina in a human for inhibiting melatonin suppression by light.

15. A device for inhibiting melatonin suppression by light comprising: means for selectively blocking more than 50 percent of incident wavelengths of light having a wavelength that suppresses melatonin production in a human and is less than at or about 530 nm, while transmitting more than 50 percent of non-blocked wavelengths of light, wherein the device inhibits melatonin suppression by light exposure when worn at night.

16. A device according to claim 15, wherein the means for selectively blocking light is an optical filter.

17. A device according to claim 16, comprising at least one of eyewear and a lens.

18. A lens operable by a user who is exposed to light at peak melatonin production times, the lens comprising an optical filter operable to selectively block more than 50 percent of incident wavelengths of light having a wavelength that suppresses melatonin production in a human and is less than at or about 530 nm, while transmitting more than 50 percent of non-blocked wavelengths of light, wherein the lens inhibits melatonin suppression by light when used at peak melatonin production times at night.

19. A lens according to claim 18, wherein the lens is incorporated into eyewear.

20. A lens according to claim 19, wherein the eyewear is selected from the group consisting of spectacles, goggles, contact lenses and safety glasses.

21. A method for inhibiting melatonin suppression by light in a human comprising providing the device according to claim 15 during peak melatonin production times thereby selectively blocking more than 50 percent of incident wavelengths of light having a wavelength that suppresses melatonin production in a human and is less than at or about 530 nm, while transmitting more than 50 percent of non-blocked wavelengths of light, the device being operable to selectively block light having a wavelength that suppresses melatonin production in a human, and is less than at or about 530 nm, from reaching the retina in a human.

22. A method for inhibiting melatonin suppression by light in a human comprising providing the lens according to claim 18 during peak melatonin production times thereby selectively blocking more than 50 percent of incident wavelengths of light having a wavelength that suppresses melatonin production in a human and is less than at or about 530 nm, while transmitting more than 50 percent of non-blocked wavelengths of light, the lens being operable to selectively block light having a wavelength that suppresses melatonin production in a human, and is less than at or about 530 nm, from reaching the retina in a human.

* * * * *